United States Patent
Jahagirdar et al.

(10) Patent No.: US 10,137,114 B2
(45) Date of Patent: Nov. 27, 2018

(54) RIFAXIMIN READY-TO-USE SUSPENSION

(71) Applicant: Lupin Limited, Mumbai (IN)

(72) Inventors: Harshal Anil Jahagirdar, Maharashtra (IN); Kishore Kumar Konda, Maharashtra (IN); Satish Kumar Dalal, Maharashtra (IN); Shirishkumar Kulkarni, Maharashtra (IN)

(73) Assignee: LUPIN LIMITED (IN)

( * ) Notice: Subject to any disclaimer, the term of this patent is extended or adjusted under 35 U.S.C. 154(b) by 0 days.

(21) Appl. No.: 14/937,730

(22) Filed: Nov. 10, 2015

(65) Prior Publication Data

US 2016/0136141 A1    May 19, 2016

Related U.S. Application Data

(63) Continuation of application No. 13/583,769, filed as application No. PCT/IB2011/000505 on Mar. 9, 2011, now Pat. No. 9,211,258.

(30) Foreign Application Priority Data

Mar. 10, 2010   (IN) .............. 233/KOL/2010

(51) Int. Cl.
| | | |
|---|---|---|
| *A61K 31/437* | (2006.01) | |
| *A61K 9/10* | (2006.01) | |
| *A61K 31/428* | (2006.01) | |
| *A23L 27/00* | (2016.01) | |

(52) U.S. Cl.
CPC ............ *A61K 31/437* (2013.01); *A23L 27/00* (2016.08); *A61K 9/10* (2013.01); *A61K 31/428* (2013.01); *A23V 2002/00* (2013.01)

(58) Field of Classification Search
CPC ...... A61K 31/437; A61K 9/10; A61K 31/428; A23L 27/00
See application file for complete search history.

(56) References Cited

FOREIGN PATENT DOCUMENTS

| WO | 02/45691 A2 | 6/2002 |
|---|---|---|
| WO | 2006/094737 A2 | 9/2006 |
| WO | 2009/008005 A1 | 1/2009 |

OTHER PUBLICATIONS

Cober, "Stability of Extemporaneously Prepared Rifaximin Oral Suspensions", American Journal of Health-System Pharmacy, 2010, 67(4), pp. 287-289.*
Brochure for Ora-Plus®—Oral Suspending Vehicle, Perrigo Pharmaceuticals.
Brochure for Ora-Sweet®—Flavored Syrup Vehicle, Paddock Laboratories, LLC.
Brochure for Ora-Blend®—Flavored Oral Suspending Vehicle, Paddock Laboratories, LLC.
Brochure for Ora-Blend® SF—Flavored Sugar-Free Oral Suspending Vehicle, Paddock Laboratories, LLC.

* cited by examiner

*Primary Examiner* — Sahar Javanmard
(74) *Attorney, Agent, or Firm* — Toan P. Vo; Bass, Berry & Sims PLC; Janelle D. Waack

(57) ABSTRACT

A stable, taste-masked, ready-to-use suspension comprising rifaximin dispersed in a suspension base and one or more pharmaceutically acceptable additive(s). Also provided is a process for preparing a stable, taste-masked, ready-to-use suspension of rifaximin comprising the steps of mixing rifaximin with the suspension base and further sizing the particles of rifaximin by milling the suspension to obtain a homogenously dispersed rifaximin suspension.

15 Claims, No Drawings

RIFAXIMIN READY-TO-USE SUSPENSION

FIELD OF THE INVENTION

The present invention pertains to a stable, taste-masked, ready-to-use suspension of rifaximin and the process for preparing it.

BACKGROUND OF THE INVENTION

The antibiotic rifaximin was originally disclosed in Italy as IT Patent 1154655. The related U.S. Pat. No. 4,341,785 to Marchi et al. discloses imidazo-rifamicyn derivatives having antibacterial utility, and the related process for preparing it. The US '785 patent also discloses a pharmaceutical antibacterial composition and a method of using it to treat antibacterial diseases of the gastrointestinal tract (GIT).

Rifaximin is essentially a low-solubility, non-absorbable, non-systemic, semi-synthetic antibiotic, related to rifamycin. The antimicrobial spectrum (in vitro) includes most gram-positive and gram-negative bacteria; and both aerobes and anaerobes. Rifaximin is approved in certain countries for the treatment of pathologies whose etiology is in part or totally due to intestinal acute and chronic infections sustained by gram-positive and gram-negative bacteria, with diarrhea syndromes, altered intestinal microbial flora, summer diarrhea-like episodes, traveler's diarrhea and enterocolitis; pre- and post- surgery prophylaxis of the infective complications in gastro intestinal surgery; and hyperammonaemia therapy as coadjutant. The drug has been found to have no significant side effects.

Rifaximin is currently marketed as tablets at the dosage of 200 mg for traveller's diarrhea under the brand name "Xifaxan®".

The most common dosage forms currently employed for oral administration of active substances are tablets and capsules. However, in recent years awareness of the drawbacks of using these dosage forms has increased. Thus, tablets and capsules are generally less suitable for administering of an active substance to pediatric and geriatric patients for whom tablets or capsules are difficult to ingest, or the large dosages necessitate the administration of several tablets or capsules at a time, resulting in impaired patient compliance.

In such situations, oral liquid dosage forms are the preferred choice. However, these dosage forms usually lead to perceptible exposure of the active drug ingredient to the taste buds, which is a very serious problem when the drug has an unpleasant or bitter taste.

The unpleasant or bitter taste of the drugs, which are orally administered, is disadvantageous in several aspects. Taste is an important parameter governing the compliance. The disagreeable and unpleasant taste of drugs causes difficulties in swallowing or causes patients to avoid their medication, thereby resulting in low patient compliance. Thus, taste-masking technologies are considered important and are developed by many researchers.

Another problem associated with an active to be formulated in a liquid dosage form is its low solubility which further affects the dissolution, potency of the drug and onset time, the potency and onset time depends on the dissolution rate of the drug.

Liquid dosage forms may be formulated as powders or granules to be reconstituted before administration, powders or granules to be admixed with a liquid in a container such as a glass before administration, thereby overcoming the difficulties involved in administering an active substance in tablet or capsule form. However, with such a formulation other problems arise, especially when the active substance in question is not dissolved in the liquid, but is present in particulate form. In such cases, the particles tend to sink to the bottom of the glass and stay there even when the contents of the glass are stirred before the glass is upended for ingestion of the liquid or to adhere to the sides of the glass when the liquid is ingested. In this way a certain amount of the active substance will remain in the glass giving rise to an unacceptable variation in the dosage of the active substance actually ingested by those to whom it is administered in this form. Furthermore, such granules or particles often have an unpleasant feel in the mouth as they typically have an irregular shape which makes them feel gritty, and they also tend to adhere to oral mucosa after the liquid carrier has been washed down. Such a dosage form therefore also tends to lead to reduced patient compliance.

CN1485034A describes rifaximin suspension which has granules for reconstitution with good taste.

The reconstitutable granules for suspension have many disadvantages such as reduced patient compliance and further there are chances for dose variation and stability problems.

In light of the above disadvantages, still there is a need to develop rifaximin suspension which can overcome the above disadvantages.

We have now found that rifaximin can be formulated in the form of ready-to-use suspension, with an improved taste, stability and solubility by careful manipulation of the flavouring agent, sweetening agent and particle size. Such formulations are envisaged to fulfill the existing need of patient friendly dosage forms especially for the pediatric and geriatric patient populations. Further, this ready-to-use suspension has many advantages over the reconstituted granules for suspension that it has improved patient compliance, improved stability and there is no dose variation while administration of ready-to-use suspension.

OBJECT OF THE INVENTION

An object of the invention is to provide a stable, taste-masked, ready-to-use suspension of rifaximin and one or more pharmaceutically acceptable additives.

Another object of the invention is to provide a stable, taste-masked ready-to-use suspension of rifaximin comprising a particle size such that $d_{90}$ is less than about 40 µm.

Yet another object of the invention is to provide a process for preparing a stable, taste-masked, ready-to-use suspension of rifaximin comprising the steps of mixing rifaximin with the suspension base and further sizing the particles of rifaximin by milling the suspension to obtain a homogenously dispersed rifaximin suspension

DETAILED DESCRIPTION OF THE INVENTION

The present invention concerns an oral, stable, pharmaceutical ready-to-use suspension of rifaximin. The suspension dosage form is capable of masking the taste of the drug and also provides the drug in a suitable form to dissolve thereby providing patient compliance, especially for children and the elderly.

The term "rifaximin" as used in the invention is meant to cover crystalline rifaximin in the form of freebase or its pharmaceutically acceptable salt(s), hydrate(s), solvate(s) and physiologically functional derivative(s) and precursors thereof. The term also includes all polymorphic forms not limited to e.g.: alpha, beta, gamma as pure or mixtures thereof.

Rifaximin may be used as a single active agent, or may be combined with other active agents, vitamins, minerals, dietary supplements, etc.

The phrase 'pharmaceutically acceptable' as used in the invention is meant to refer to those compounds, materials compositions, or other dosage forms that are, within the scope of medical judgment, suitable for use in contact with tissues of human beings and animals and without excessive toxicity, irritation, allergic response, or any other problem or complication.

The term 'ready-to-use' as used in the present invention means admixture of the particles comprising the active substance with suspension base.

The term 'taste masking' as used in the invention is meant to refer as reduction of perceptible unpleasant taste associated with Rifaximin in the pharmaceutical composition and/or after stability.

The term 'stable' as used in the present invention relates to both chemical (shelf-life) and physical stability (suspension uniformity). Improved uniformity results in an improved product because less shaking of the suspension is required before dosing and allows the product to be stored longer (i.e. longer shelf-life) because the drug in the product will not settle and compact.

For the purposes of the present invention, rifaximin is milled or micronized in the suspension. In order to produce rifaximin suspension having the desired particle size, the suspension is milled by various techniques for example conventional commutation and deagglomeration, grinding in an air-jet mill or impact mill, a ball mill, dry milling, wet milling, colloidal mill, dyano mill and micronization, microfluidization techniques may be used. Using the above techniques helps in obtaining the desired particle size with increased wettability, solubility and dissolution of Rifaximin.

Small particle size is desirable for reasons other than slowing the rate of sedimentation. For drugs that are not very soluble, smaller particles generally dissolve faster due to the increase in the total surface area. Also, smaller drug particles are less likely to cause grittiness, which improves the palatability of the finished product. There is therefore a need for a suspension containing fine particles, hereafter referring to $d_{90}$ less than about 40 µm, which will not cake on storage, but in addition is able to maintain its homogeneity on prolonged storage.

The term '$d_{90}$' as used herein means that "90% particles is less than about 40um". It is noted that the notation $d_x$ means that X % of particles have a diameter less than the specified diameter d.

The $d_{90}$ of the rifaximin dispersed or suspended in the suspension is less than about 40 µm and more preferably of less than about 20 µm.

The particle size of the rifaximin particles is measured for the purpose of this invention using light scattering technique (Malvern Mastersizer Hydro 2000S).

Another important property of the suspension is viscosity which further plays a role in the stability of suspension that is it helps in slowing the sedimentation rate of suspension. It is desired that in the present invention, the viscosity of the suspension should not be so high that pumping and handling would be difficult in industrial practice, but high enough to confer upon the suspension stability to settling of suspended particles for a reasonable period of time. The viscosity of the suspension should be such that it provides a pourable consistency to the suspension. Preferably, the suspension of the present invention has a viscosity in the range of about 20 cps to about 200 cps when measured by Brookfield viscometer at room temperature and 100 RPM using spindle no. 2.

The taste-masked, ready-to-use suspension according to the invention has a suspension base with the active ingredient dispersed in the suspension base. The pharmaceutically acceptable suspension base may be, for example, an aqueous solvent such as water, with the suspending/viscosity enhancing agent dispersed throughout. The pharmaceutically acceptable suspension base may contain various additive(s) which are known to a skilled person in art.

The taste-masked, ready-to-use suspension of rifaximin, or a pharmaceutically acceptable salt(s) according to present invention further comprises at least one or more other pharmaceutically acceptable additive(s) selected from group comprising but not limited to flavouring agent(s), sweetening agent(s), buffering agent(s), preservative(s), suspending agent(s), antioxidant(s), wetting agent(s), dispersing agent(s), pH stabilizing agent(s), taste enhancing agent(s), antifoaming agent(s) and mixtures thereof.

An additive can serve multiple functions.

Flavoring agent(s) used in the invention is meant to impart a pleasant flavor and/or odor to a pharmaceutical composition. Suitable flavoring agents include but not limited to natural and artificial flavors, such as synthetic flavor oils and flavoring aromatics and/or natural oils, extracts from plants, leaves, flowers, fruits and so forth and combinations thereof. Representative suitable flavoring agents may be for example, without limitation, menthol, cinnamon, wintergreen, clove, bay, anise, eucalyptus, thyme, cedar leave, nutmeg, sage, bitter almonds and cassia, vanilla, artificial vanilla, chocolate, artificial chocolate, bubble gum, both natural and artificial fruit flavors, such as cherry flavor, grape flavor, orange flavor, banana flavor, strawberry flavor, lemon flavor, grapefruit flavor and "mint" flavors such as peppermint flavor and spearmint flavor, lime flavor, apple flavor, pear flavor, peach flavor, raspberry flavor, plum flavor, pineapple flavor, apricot flavor and so forth, including combinations of two or more thereof. Flavoring agents are generally provided as a minor component of the composition in amounts effective to provide a palatable flavor to the composition. The amount of flavoring agent may depend on a number of factors, including the desired organoleptic effect. The precise amount of sweetening and/or flavoring agent(s) depends on the properties of the agent(s) used, however generally in an amount that is sufficient to mask the unpleasant taste and/or odor associated with rifaximin as determinable by one skilled in the art. However, flavoring agents generally present is in a pharmaceutically acceptable range.

Sweeteners suitable for inclusion in the present invention may be determined by one skilled in the art including, for example without limitation, both natural and artificial sweeteners such as the representative sweetening agents of intense sweeteners such as sorbitol, sucrose, saccharins such as sodium saccharin, cyclamates such as sodium cyclamates, aspartame, sucralose, thaumatin, acesulfam K, and the like, and sugars such as monosaccharides, disaccharides and polysaccharides. Representative sugars useful in the present invention include, without limitation, xylose, ribose, glucose, mannose, galactose, fructose, dextrose, sucrose, maltose, partially hydrolyzed starch or corn syrup, and sugar alcohols such as sorbitol, xylitol, mannitol, glycerin, etc. and combination thereof. Presently preferred as a sugar sweetener is sucralose. Sugar sweeteners may be replaced or augmented by water-soluble artificial sweeteners, such as the suitable artificial sweeteners previously listed and mixtures thereof. The amount of artificial sweetener used in the composition may vary to provide an appropriate amount of sweetness as determinable by one skilled in the art. Mixtures of sweetening and/or flavoring agents are preferably used.

By suitable combination of sweetener and flavouring agents the unpleasant taste of the rifaximin can be improved.

Examples of preservatives suitable for use in the present invention include, for example without limitation, one or more alkyl hydroxybenzoates, such as methyl hydroxybenzoates, ethyl hydroxybenzoates, propyl hydroxybenzoates, butyl hydroxybenzoates and the like. Additional preservatives useful in the present invention include, but are not limited to, sodium benzoate, potassium sorbate, salts of edetate (also known as salts of ethylenediaminetetraacetic acid or EDTA, such as disodium edetate) and antimicrobial agents including parabens (p-hydroxybenzoic acids esters) such as methyl paraben, ethylparaben, propylparaben, butylparaben and the like, and combinations thereof. Parabens are preferred, with methyl paraben most preferred for use as preservative ingredients to add to the present pharmaceutical composition, although other pharmaceutically acceptable preservatives may be substituted therefore. Preservative(s) as used in the composition are in a pharmaceutically acceptable range.

Examples of suspending/viscosity agents suitable for use in the present invention include but are not limited to gums; sorbitol; glycerol; polyvinyl alcohol; polyvinyl pyrrolidone; polyethylene oxide; cellulose derivatives, such as hydroxypropylmethylcellulose or a salt thereof, alkyl ether of cellulose, such as methylcellulose, ethylcellulose, hydroxyethylcellulose, hydroxyethylmethylcellose and mixtures thereof. Preferably the viscosity-enhancing agent is hydroxypropylmethylcellulose e.g. (HPMC K4M, HPMC K100 LVP; HPMC K15MP; HPMC E4 MP; HPMC E10 MP CR).

The pharmaceutical composition may also contain a dispersing agent(s), which include but are not limited to, colloidal silicon dioxide and surfactants, wherein the surfactant is used alone or as an admixture with one or more surfactant. Combinations of colloidal silicon dioxide with one or more surfactants can also be used and other pharmaceutically accepted dispersing agents.

The pharmaceutical composition may also contain a pH stabilizing agent to maintain a desired pH. The term "pH stabilizing agent" encompasses buffers, suitable pH stabilizing agents include but not limited to tribasic sodium phosphate, anhydrous sodium carbonate, glycine, citric acid or mixtures thereof.

Preferably, the pH of the composition is in range of about 2.0 about 8.0. Most preferably the pH of composition is in range from about 4.5 to about 6.0.

The pharmaceutical composition may also contain wetting agent(s) which include, but are not limited to such as sorbitan monolaurate, polysorbate 80, and sodium lauryl sulfate and the like.

The pharmaceutical composition may also contain suitable coloring agent(s) to provide an appealing color to the pharmaceutical composition, which include, but are not limited to, titanium dioxide pigments, lake colors and iron oxide pigments.

The pharmaceutical ready-to-use suspension composition may also contain suitable antifoaming agents, which include, but are not limited to simethicone emulsion, dimethicone, lutrol and the like.

The pharmaceutical composition may also contain antioxidant(s) which include, but are not limited to such as tocopherols, gallic acid and gallates, butylated hydroxy anisole, butylated hydroxy toluene, ascorbic acid, maleic acid, sodium bisulphate, sodium metabisulphite, sodium-formaldehyde sulphoxylate and the like.

All these additive(s) can be used at levels well known to the persons skilled in the art.

The ready-to-use suspension of rifaximin can be prepared by a process comprising the steps of mixing Rifaximin with one or more additive(s) selected from the group comprising stabilizers, wetting agents, sweeteners, thickening agents, dispersing agents, pH stabilizing agents, flavoring agents, preservatives, coloring agents, and the like. Further, it is mixed with suspension vehicles well known to persons skilled in the art, such as xylitol, propylene glycol, glycerin, sorbitol, liquid glucose and the like in addition to water and further milling the above suspension.

The above specifically mentioned pharmaceutically acceptable additive(s) are intended to be exemplary, not exhaustive; other additives may also be used in the practice of the disclosed invention. It is further understood that more than one of any particular type of additive may be used in the compositions described herein. For example, the compositions may include more than one flavorant, colorant, etc.

The following examples are illustrative of the present invention, and the examples should not be considered as limiting the scope of this invention in any way, as these examples and other equivalents thereof will become apparent to those versed in the art, in the light of the present disclosure, and the accompanying claims:

EXAMPLES

Example 1

| Sr. No. | Ingredients | % w/w |
| --- | --- | --- |
| 1. | Rifaximin | 2.00 |
| 2. | Sucrose | 45.00 |
| 3. | Sorbitol 70% | 10.00 |
| 4. | Propylene glycol | 10.00 |
| 5. | Polysorbate 80 | 10.00 |
| 6. | Sodium citrate | 1.00 |
| 7. | Citric acid | 0.35 |
| 8. | Methyl Paraben | 0.175 |
| 9. | Propyl Paraben | 0.18 |
| 10. | Xanthan gum | 0.10 |
| 11. | Sodium saccharin | 0.001 |
| 12. | Flavor | 1.00 |
| 13. | Purified water | Up to 100 |

Procedure:

1. Take required quantity (qty) of purified water and boil. To this add required quantity of sucrose to form a clear solution and cool.
2. To step 1, add weighed quantity of sorbitol and polysorbate 80 under stirring.
3. Add Rifaximin to propylene glycol followed by Methyl paraben and Propyl paraben to form slurry and add to step 2, under stirring.
4. Take required qty. of purified water and soak Xanthan gum until it forms a colloidal dispersion.
5. Take required qty. of water, to this add sodium saccharin and sodium citrate to form a clear solution and add to step 4, under stirring.

6. Pass step 5 through colloidal mill.
7. Add required qty. of flavour to step 6 under stirring.
8. Adjust the pH to 5.5 using citric acid and make up the volume.

Example 2

| Sr. No. | Ingredients | % w/w |
|---|---|---|
| 1. | Rifaximin | 2.00 |
| 2. | Sucrose | 45.00 |
| 3. | Sorbitol 70% | 10.00 |
| 4. | Propylene glycol | 10.00 |
| 5. | Polysorbate 80 | 10.00 |
| 6. | Sodium citrate | 1.00 |
| 7. | Citric acid | 0.35 |
| 8. | Methyl Paraben | 0.175 |
| 9. | Propyl Paraben | 0.18 |
| 10. | Xanthan gum | 0.100 |
| 11. | Sucralose | 0.001 |
| 12. | Flavor | 1.00 |
| 13. | Purified water | Up to 100 |

Procedure:
1. Take required qty. of purified water and boil. To this add required quantity of sucrose to form a clear solution and cool.
2. To step 1, add weighed quantity of sorbitol and polysorbate 80 under stirring.
3. Add Rifaximin to propylene glycol followed by Methyl paraben and Propyl paraben to form slurry and add to step 2, under stirring.
4. Take required qty. of purified water and soak Xanthan gum until it forms a colloidal dispersion.
5. Take required qty. of water to this add sucralose and sodium citrate to form a clear solution and add to step 4, under stirring.
6. Pass step 5 through colloidal mill.
7. Add required qty. of flavour to step 6 under stirring.
8. Adjust the pH to 5.5 using citric acid and make up the volume.

Example 3

| Sr. No. | Ingredients | % w/w |
|---|---|---|
| 1. | Rifaximin | 2.00 |
| 2. | Xylitol | 45.00 |
| 3. | Sorbitol 70% | 10.00 |
| 4. | Propylene glycol | 10.00 |
| 5. | Polysorbate 80 | 10.00 |
| 6. | Sodium citrate | 1.00 |
| 7. | Citric acid | 0.35 |
| 8. | Methyl Paraben | 0.175 |
| 9. | Propyl Paraben | 0.18 |
| 10. | Xanthan gum | 0.10 |
| 11. | Sucralose | 0.001 |
| 12. | Flavor | 1.00 |
| 13. | Purified water | Up to 100 |

Procedure:
1. Take required qty. of purified water and boil to this add required quantity of sucrose to form a clear solution and cool.
2. To step 1, add weighed quantity of sorbitol and polysorbate 80 under stirring.
3. Add Rifaximin to propylene glycol followed by Methyl paraben and Propyl paraben to form slurry and add to step 2, under stirring.
4. Take required qty. of purified water and soak Xanthan gum until it forms a colloidal dispersion.
5. Take required qty. of water to this add sucralose and sodium citrate to form a clear solution and add to step 4, under stirring.
6. Pass step 5 through colloidal mill.
7. Add required qty. of flavour to step 6 under stirring.
8. Adjust the pH to 5.5 using citric acid and make up the volume.

Example 4

| Sr. No. | Ingredients | % w/w |
|---|---|---|
| 1. | Rifaximin | 2.00 |
| 2. | Xylitol | 40.00 |
| 3. | Sorbitol 70% | 20.00 |
| 4. | Propylene glycol | 10.00 |
| 5. | Polysorbate 80 | 1.00 |
| 6. | Sodium citrate | 0.35 |
| 7. | Citric acid | 0.175 |
| 8. | Methyl Paraben | 0.18 |
| 9. | Propyl Paraben | 0.02 |
| 10. | Xanthan gum | 0.10 |
| 11. | Sucralose | 0.001 |
| 12. | Glycerin | 5.00 |
| 13. | Silicon dioxide | 0.10 |
| 14. | Purified water | Up to 100 |

Procedure:
1. Take required qty. of purified water and boil to this add required quantity of sucrose to form a clear solution and cool.
2. To step 1, add weighed quantity of sorbitol and polysorbate 80 under stirring.
3. Add Rifaximin to propylene glycol followed by Methyl paraben and Propyl paraben to form slurry and add to step 2, under stirring.
4. Take required qty. of purified water and soak Xanthan gum until it forms a colloidal dispersion.
5. Take required qty. of water to this add sucralose and sodium citrate to form a clear solution and add to step 4, under stirring.
6. Add step 5 to step 3 under stirring.
7. Pass step 6 through colloidal mill.
8. Add required qty. of flavour to step 7 under stirring.
9. Adjust the pH to 5.5 using citric acid and make up the volume.

Example 5

| Sr. No. | Ingredients | % w/w |
|---|---|---|
| 1. | Rifaximin | 2.00 |
| 2. | Sucrose | 45.00 |
| 3. | Sorbitol 70% | 10.00 |
| 4. | Propylene glycol | 10.00 |
| 5. | Polysorbate 80 | 10.00 |
| 6. | Sodium citrate | 1.00 |
| 7. | Ascorbic acid | 0.35 |
| 8. | Methyl Paraben | 0.175 |
| 9. | Propyl Paraben | 0.18 |
| 10. | Xanthan gum | 0.10 |

-continued

| Sr. No. | Ingredients | % w/w |
|---|---|---|
| 11. | Sodium saccharine | 0.001 |
| 12. | Flavor | 1.00 |
| 13. | Purified water | Up to 100 |

Procedure:
1. Take required qty. of purified water and boil to this add required quantity of sucrose to form a clear solution and cool.
2. To step 1, add weighed quantity of sorbitol and polysorbate 80 under stirring.
3. Add Rifaximin to propylene glycol followed by Methyl paraben and Propyl paraben to form slurry and add to step 2, under stirring.
4. Take required qty. of purified water and soak Xanthan gum until it forms a colloidal dispersion.
5. Take required qty. of water to this add Ascorbic acid, sodium saccharin and sodium citrate to form a clear solution and add to step 4, under stirring.
6. Add step 5 to step 3 under stirring.
7. Pass step 6 through colloidal mill.
8. Add required qty. of flavour to step 7 under stirring.
9. Adjust the pH to 5.5 using citric acid and make up the volume.

Example 6

| Sr. No. | Ingredients | % w/w |
|---|---|---|
| 1. | Rifaximin | 2.00 |
| 2. | Sucrose | 45.00 |
| 3. | Sorbitol 70% | 10.00 |
| 4. | Propylene glycol | 10.00 |
| 5. | Polysorbate 80 | 10.00 |
| 6. | Sodium citrate | 1.00 |
| 7. | Ascorbic acid | 0.35 |
| 8. | Methyl Paraben | 0.175 |
| 9. | Propyl Paraben | 0.18 |
| 10. | Hypromellose | 0.10 |
| 11. | Sodium saccharine | 0.001 |
| 12. | Flavor | 1.00 |
| 13. | Purified water | Up to 100 |

Procedure:
1. Take required qty. of purified water and boil to this add required quantity of sucrose to form a clear solution and cool.
2. To step 1, add weighed quantity of sorbitol and polysorbate 80 under stirring.
3. Add Rifaximin to propylene glycol followed by Methyl paraben and Propyl paraben to form slurry and add to step 2, under stirring.
4. Take required qty. of purified water and add Hypromellose so it forms a colloidal dispersion.
5. Take required qty. of water to this add Ascorbic acid, sodium saccharin and sodium citrate to form a clear solution and add to step 4, under stirring.
6. Add step 5 to step 3 under stirring.
7. Pass step 6 through colloidal mill.
8. Add required qty. of flavour to step 7 under stirring.
9. Adjust the pH to 5.5 using citric acid and make up the volume.

Example 7

| Sr. No. | Ingredients | % w/w |
|---|---|---|
| 1. | Rifaximin | 2.00 |
| 2. | Sucrose | 45.00 |
| 3. | Sorbitol 70% | 10.00 |
| 4. | Propylene glycol | 10.00 |
| 5. | Polysorbate 80 | 10.00 |
| 6. | Sodium citrate | 1.00 |
| 7. | Citric acid | 0.35 |
| 8. | Methyl Paraben | 0.175 |
| 9. | Propyl Paraben | 0.18 |
| 10. | Sodium Carboxymethyl cellulose | 0.10 |
| 11. | Sodium saccharine | 0.001 |
| 12. | Flavor | 1.00 |
| 13. | Purified water | Up to 100 |

Procedure:
1. Take required qty. of purified water and boil to this add required quantity of sucrose to form a clear solution and cool.
2. To step 1, add weighed quantity of sorbitol and polysorbate 80 under stirring.
3. Add Rifaximin to propylene glycol followed by Methyl paraben and Propyl paraben to form slurry and add to step 2, under stirring.
4. Take required qty. of purified water and add Sodium Carboxymethyl cellulose so it forms a colloidal dispersion.
5. Take required qty. of water to this add sodium saccharin and sodium citrate to form a clear solution and add to step 4, under stirring.
6. Add step 5 to step 3 under stirring.
7. Pass step 6 through colloidal mill.
8. Add required qty. of flavour to step 7 under stirring.
9. Adjust the pH to 5.5 using citric acid and make up the volume.

Example 8

| Sr. No. | Ingredients | % w/w |
|---|---|---|
| 1. | Rifaximin | 2.00 |
| 2. | Sucrose | 45.00 |
| 3. | Sorbitol 70% | 10.00 |
| 4. | Propylene glycol | 10.00 |
| 5. | Polysorbate 80 | 10.00 |
| 6. | Sodium citrate | 1.00 |
| 7. | Citric acid | 0.35 |
| 8. | Methyl Paraben | 0.175 |
| 9. | Propyl Paraben | 0.18 |
| 10. | Gum Arabic | 0.10 |
| 11. | Sodium saccharine | 0.001 |
| 12. | Flavor | 1.00 |
| 13. | Purified water | Up to 100 |

Procedure:
1. Take required qty. of purified water and boil to this add required quantity of sucrose to form a clear solution and cool.
2. To step 1, add weighed quantity of sorbitol and polysorbate 80 under stirring.
3. Add Rifaximin to propylene glycol followed by Methyl paraben and Propyl paraben to form slurry and add to step 2, under stirring.

4. Take required qty. of purified water and soak Gum Arabic until it forms a colloidal dispersion.
5. Take required qty. of water to this add sodium saccharin and sodium citrate to form a clear solution and add to step 4, under stirring.
6. Add step 5 to step 3 under stirring.
7. Pass step 6 through colloidal mill.
8. Add required qty. of flavour to step 7 under stirring.
9. Adjust the pH to 5.5 using citric acid and make up the volume.

Example 9

| Sr. No. | Ingredients | % w/w |
|---|---|---|
| 1. | Rifaximin | 2.00 |
| 2. | Sucrose USP | 45.00 |
| 3. | Sorbitol 70% NC | 5.00 |
| 4. | Propylene glycol | 15.00 |
| 5. | Polysorbate 80 | 10.00 |
| 6. | Sodium citrate | 1.00 |
| 7. | Citric acid | 0.35 |
| 8. | Methyl Paraben | 0.175 |
| 9. | Propyl Paraben | 0.18 |
| 10. | Xanthan gum | 0.10 |
| 11. | Sodium saccharine | 0.001 |
| 12. | Flavor | 1.00 |
| 13. | Purified water | Up to 100 |

Procedure:
1. Take required qty. of purified water and boil to this add required quantity of sucrose to form a clear solution and cool.
2. To step 1, add weighed quantity of sorbitol and polysorbate 80 under stirring.
3. Add Rifaximin to propylene glycol followed by Methyl paraben and Propyl paraben to form slurry and add to step 2, under stirring.
4. Take required qty. of purified water and soak Xanthan gum until it forms a colloidal dispersion.
5. Take required qty. of water to this add sodium saccharin and sodium citrate to form a clear solution and add to step 4, under stirring.
6. Add step 5 to step 3 under stirring.
7. Pass step 6 through Dyno-mill by using suitable beads and carry out the milling for 10-12 cycles or till required size is obtained.
8. Add required qty. of flavour to step 7 under stirring.
9. Adjust the pH to 5.5 by using citric acid and make up the volume.

Example 10

| Sr. No. | Ingredients | % w/w |
|---|---|---|
| 1. | Rifaximin | 2.00 |
| 2. | Sucrose USP | 45.00 |
| 3. | Sorbitol_0% NC | 5.00 |
| 4. | Propylene glycol | 15.00 |
| 5. | Polysorbate 80 | 10.00 |
| 6. | Sodium citrate | 1.00 |
| 7. | Citric acid | 0.35 |
| 8. | Methyl Paraben | 0.175 |
| 9. | Propyl Paraben | 0.18 |
| 10. | Xanthan gum | 0.10 |
| 11. | Sodium saccharine | 0.001 |
| 12. | Flavor | 1.00 |
| 13. | Purified water | Up to 100 |

Procedure:
1. Take required qty. of purified water and boil to this add required quantity of sucrose to form a clear solution and cool.
2. To step 1, add weighed quantity of sorbitol and polysorbate 80 under stirring.
3. Add Rifaximin to propylene glycol followed by Methyl paraben and Propyl paraben to form slurry and add to step 2, under stirring.
4. Take required qty. of purified water and soak Xanthan gum until it forms a colloidal dispersion.
5. Take required qty. of water to this add sodium saccharin and sodium citrate to form a clear solution and add to step 4, under stirring.
6. Add step 5 to step 3 under stirring.
7. Pass step 6 through microfluidizer and carry out the milling for 10-12 cycles or till required size is obtained.
8. Add required qty. of flavour to step 7 under stirring.
9. Adjust the pH to 5.5 by using citric acid and make up the volume.

Resuspendability (Suspension Uniformity) Test

There is no compendial USP requirement for dosage uniformity of suspension. For oral solid dosage formats, the USP requirement is that the amount of the active ingredient of each dosage unit is between 85 and 115% of label claim and the relative standard deviation (RSD) of ten dosage units is less than or equal to 6.0%. We adapt this requirement with slight modifications for suspension.

A 150 ml bottle was filled with exactly 100 ml of suspension, bottle was shaken vigorously and using pipette the samples were withdrawn from the top, middle and bottom and analyzed for amount of active ingredient. The %RSD was NMT 5%, thus passing the uniformity test.

The test was performed on day 1 followed by 1 month, 2 month and 3 month at 40° C. 75% RH.

Evaluation of Taste Masking Effect: Sensory Test 20 healthy volunteers involved in the study were exposed to the taste of the Rifaximin suspension of present invention on day 1, day 7 and day 14. The suspensions were subjected to sensory test. Each of the suspension was actually put in the mouth of twenty volunteers, in an amount equivalent to 100 mg of the liquid Rifaximin. The results indicated that Example 1 and 2 has better acceptance.

Accelerated Stability Test

Accelerated Stability Studies as per ICH guidelines, have been performed for Example 2 at 40° C. 75% RH for 3 months. As per the observations made, the composition of the present invention is stable under the conditions mentioned.

| Test | Initial | 1 Month | 2 Month | 3 Month |
|---|---|---|---|---|
| | | 40° C./75% RH | | |
| Assay | 103.300% | 100.7% | 101.6% | 100.30% |
| Weight/ml | 1.21 | 1.21 | 1.21 | 1.2 |

-continued

| Test | Initial | 1 Month | 2 Month 40° C./75% RH | 3 Month |
|---|---|---|---|---|
| Related substances | | | | |
| 1. Total Impurity | 0.554% | 0.7% | 0.598% | 0.565% |
| 2. Highest Unknown Impurity | 0.083% | 0.0129% | 0.097% | 0.088% |

The invention claimed is:

1. A process for preparing a stable, taste-masked, ready-to-use suspension of rifaximin wherein the said process comprises the steps of dispersing rifaximin in a suspension base comprising one or more pharmaceutically acceptable additive(s) and further milling the suspension to obtain a homogenously dispersed rifaximin suspension; wherein the suspension has a viscosity from about 20Cps to about 200 Cps and is stable for 90 days under conditions of 40° C. and 75% relative humidity.

2. The process of claim 1, wherein the one or more pharmaceutically acceptable additive(s) are selected from the group consisting of flavoring agent(s), sweetening agent(s), buffering agents(s), preservative(s), suspending agents(s), antioxidant(s), wetting agent(s), dispersing agent(s), pH stabilizing agent(s), taste enhancing agent(s), antifoaming agent(s) and mixtures thereof.

3. The process of claim 1, wherein the pH of the suspension is from about 2 to about 8.

4. The process of claim 1, wherein the pH of the suspension is from about 4.5 to about 6.

5. The process of claim 1, wherein the $d_{90}$ of rifaximin is less than about 40μm.

6. The process of claim 1, wherein the $d_{90}$ of rifaximin is less than about 20μm.

7. A process for preparing a stable, taste-masked, ready-to-use suspension of rifaximin wherein the said process comprises the steps of dispersing rifaximin in a suspension base comprising one or more pharmaceutically acceptable additive(s) and further milling the suspension to obtain a homogenously dispersed rifaximin suspension, wherein the viscosity of the suspension is from about 20 Cps to about 200 Cps; wherein the suspension is stable for 90 days under conditions of 40° C. and 75% relative humidity.

8. The process of claim 7, wherein, wherein the one or more pharmaceutically acceptable additive(s) are selected from the group consisting of flavoring agent(s), sweetening agent(s), buffering agents(s), preservative(s), suspending agents(s), antioxidant(s), wetting agent(s), dispersing agent(s), pH stabilizing agent(s), taste enhancing agent(s), antifoaming agent(s) and mixtures thereof.

9. The process of claim 7, wherein, wherein the $d_{90}$ of rifaximin is less than about 40 μm.

10. The process of claim 7, wherein the pH of the suspension is from about 2 to about 8.

11. The process of claim 7, wherein the pH of the suspension is from about 4.5 to about 6.

12. A process for preparing a stable, taste-masked, ready-to-use suspension of rifaximin wherein the said process comprises the steps of dispersing rifaximin in the suspension base comprising one or more pharmaceutically acceptable additive(s) and further milling the suspension to obtain a homogenously dispersed rifaximin suspension, wherein the $d_{90}$ of rifaximin is less than about 40 μm ; and further wherein the suspension has a viscosity from about 20 Cps to about 200 Cps and is stable for 90 days under conditions 40° C. and 75% relative humidity.

13. The process of claim 12, wherein the one or more pharmaceutically acceptable additive(s) are selected from the group consisting of flavoring agent(s), sweetening agent(s), buffering agents(s), preservative(s), suspending agents(s), antioxidant(s), wetting agent(s), dispersing agent(s), pH stabilizing agent(s), taste enhancing agent(s), antifoaming agent(s) and mixtures thereof.

14. The process of claim 12, wherein the pH of the suspension is from about 2 to about 8.

15. The process of claim 12, wherein the pH of the suspension is from about 4.5 to about 6.

* * * * *